United States Patent [19]
McPhee

[11] Patent Number: 6,019,747
[45] Date of Patent: Feb. 1, 2000

[54] SPRING-ACTUATED INFUSION SYRINGE

[75] Inventor: Charles J. McPhee, Huntington Beach, Calif.

[73] Assignee: I-Flow Corporation, Lake Forest, Calif.

[21] Appl. No.: 08/957,970

[22] Filed: Oct. 21, 1997

[51] Int. Cl.⁷ ..................................................... A61M 5/00
[52] U.S. Cl. ........................... 604/211; 604/136; 604/232
[58] Field of Search ..................................... 604/134, 135, 604/207, 208, 209, 218, 232, 154

[56] References Cited

U.S. PATENT DOCUMENTS

| | | |
|---|---|---|
| 2,472,116 | 6/1949 | Maynes . |
| 2,565,081 | 8/1951 | Maynes . |
| 2,591,457 | 4/1952 | Maynes . |
| 3,880,163 | 4/1975 | Ritterskamp . |
| 3,882,863 | 5/1975 | Sarnoff et al. . |
| 4,316,463 | 2/1982 | Schmitz et al. . |
| 4,381,006 | 4/1983 | Genese . |
| 4,530,695 | 7/1985 | Phillips et al. . |
| 4,597,754 | 7/1986 | Thill et al. . |
| 4,623,330 | 11/1986 | Laby et al. . |
| 4,755,172 | 7/1988 | Baldwin . |
| 4,966,585 | 10/1990 | Gangemi . |
| 4,997,420 | 3/1991 | LeFevre . |
| 5,078,679 | 1/1992 | Reese . |
| 5,100,389 | 3/1992 | Vaillancourt . |
| 5,178,609 | 1/1993 | Ishikawa . |
| 5,300,030 | 4/1994 | Crossman et al. ................... 604/134 X |
| 5,318,539 | 6/1994 | O'Neil . |
| 5,320,609 | 6/1994 | Haber et al. . |
| 5,330,435 | 7/1994 | Sullivan . |
| 5,383,858 | 1/1995 | Reilly et al. . |
| 5,425,715 | 6/1995 | Dalling et al. ....................... 604/135 X |
| 5,599,309 | 2/1997 | Marshall et al. ..................... 604/134 X |
| 5,599,315 | 2/1997 | McPhee .................................. 604/218 |
| 5,800,405 | 9/1998 | McPhee .................................. 604/218 |

FOREIGN PATENT DOCUMENTS

| | | |
|---|---|---|
| 0584569 | 2/1994 | European Pat. Off. . |
| 624958 | 6/1949 | United Kingdom . |
| 94/07553 | 4/1994 | WIPO . |
| WO9407553 | 4/1994 | WIPO . |
| 95/00193 | 1/1995 | WIPO . |
| WO9500193 | 1/1995 | WIPO . |

Primary Examiner—Wynn Wood Coggins
Assistant Examiner—A. T. Nguyen
Attorney, Agent, or Firm—Klein & Szekeres, LLP

[57] ABSTRACT

A spring-actuated infusion syringe includes a housing having an open distal end, with a spring-loaded piston disposed for axial translation in the housing. The piston is biased toward the distal end of the housing. The syringe also includes a barrel for containing a liquid medicament, the barrel having a distal end having a fluid passage therethrough and an open proximal end. A plunger is disposed in the barrel for axial translation therein. The proximal end of the barrel is axially insertable into the distal end of the housing, whereby the piston enters the proximal end of the barrel and engages the plunger. In use, the barrel is filled with a medicament through the fluid flow passage, and the flow of medicament from the syringe is obstructed. The proximal end of the barrel is inserted into the distal end of the housing, whereby the piston enters the proximal end of the barrel. The plunger, immobilized by the hydrostatic pressure of the liquid in the barrel, pushes the piston proximally against its biasing force. An engagement between an annular barrel flange and an internal housing thread retains the barrel at the desired axial position within the housing. To deliver the liquid from the syringe, the obstruction is removed. The hydrostatic pressure in the barrel being relieved, the biasing force of the piston pushes the plunger distally into the barrel, displacing the liquid therefrom through the fluid flow passage.

16 Claims, 3 Drawing Sheets

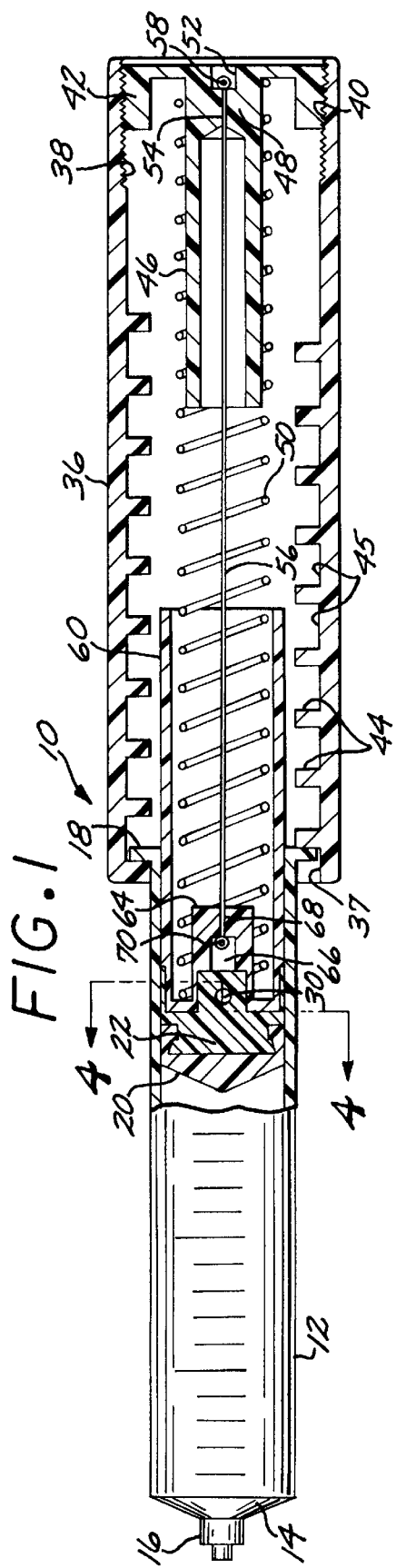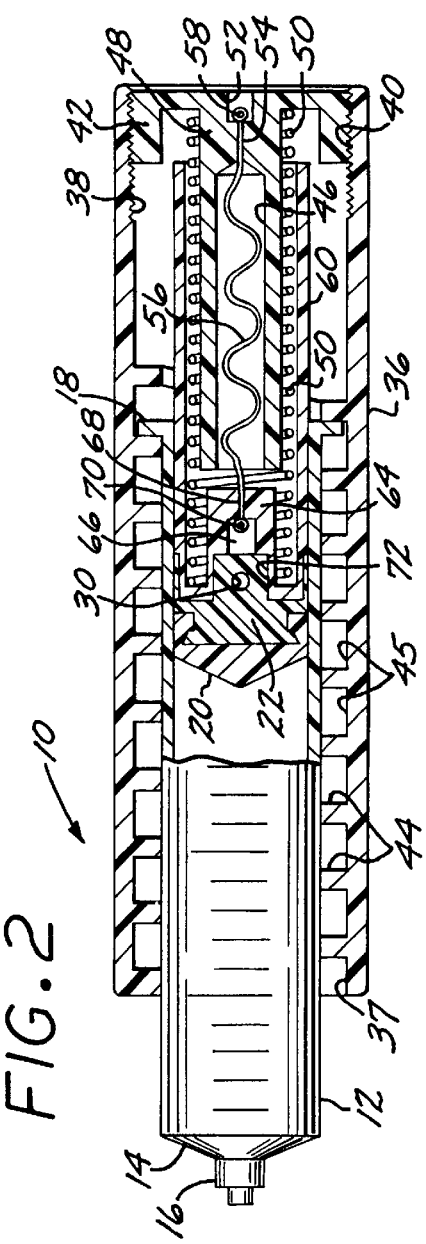

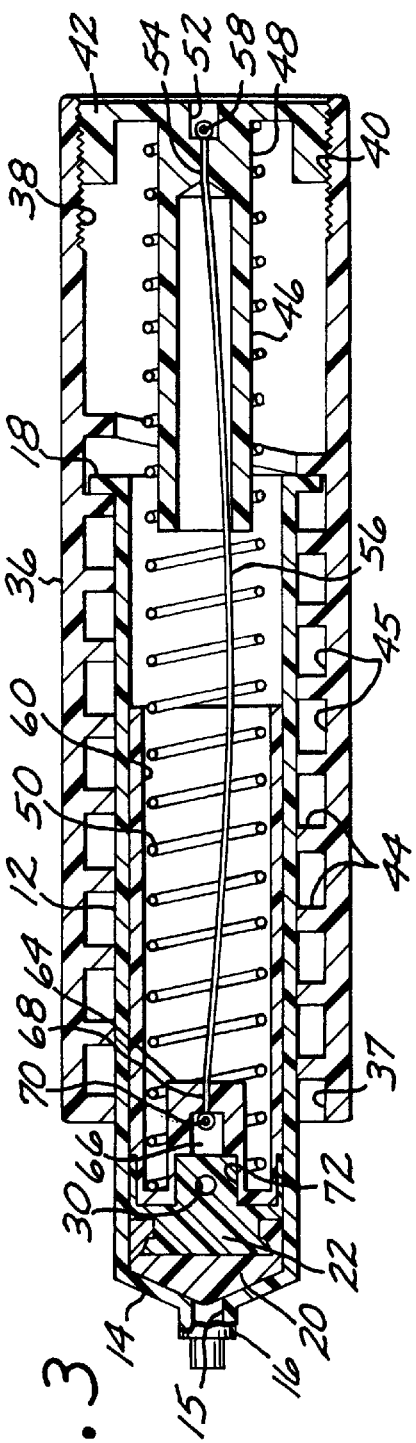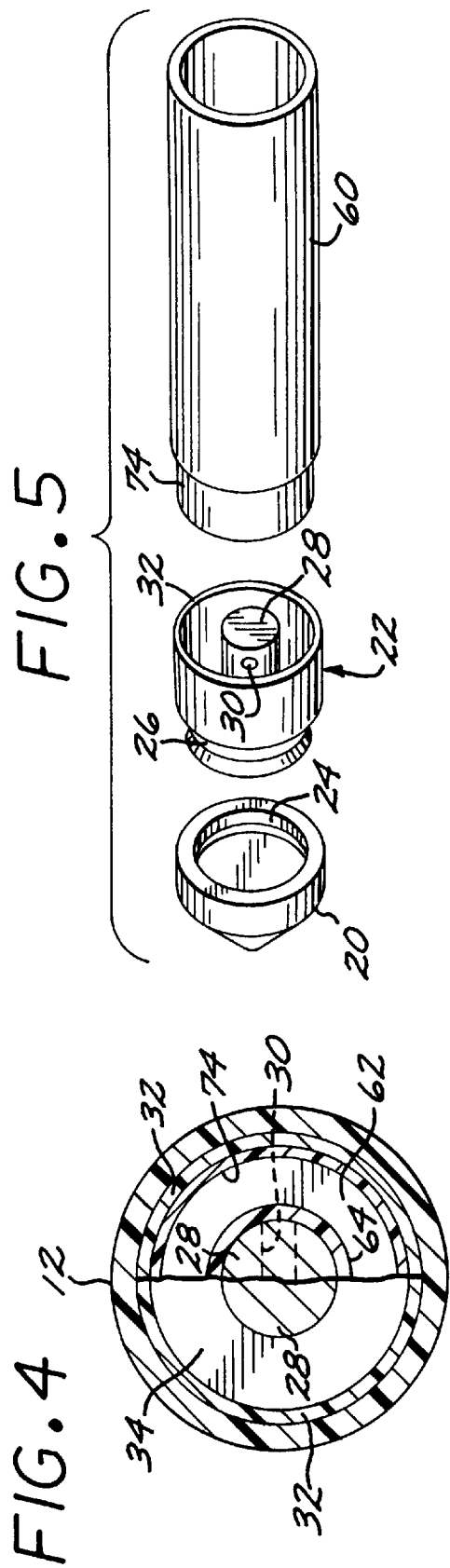

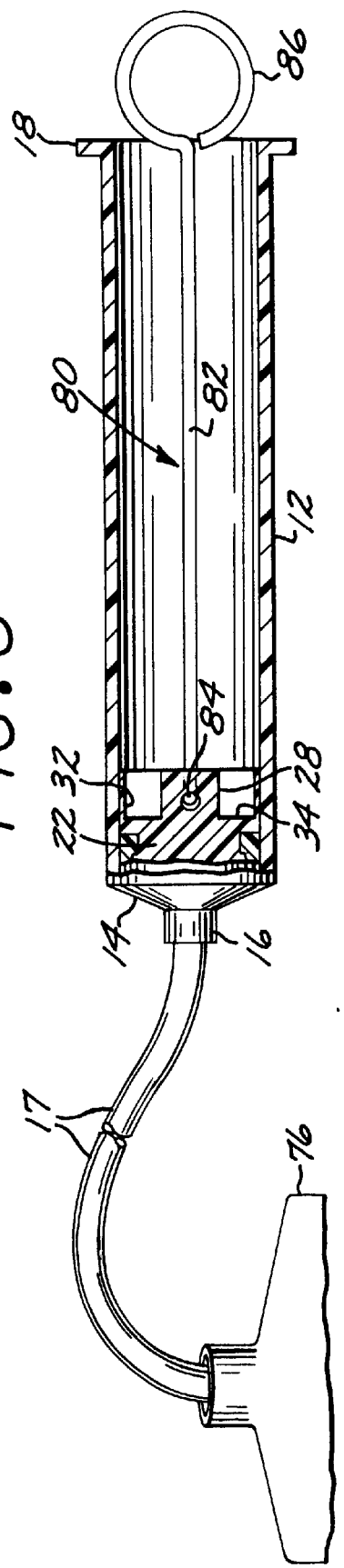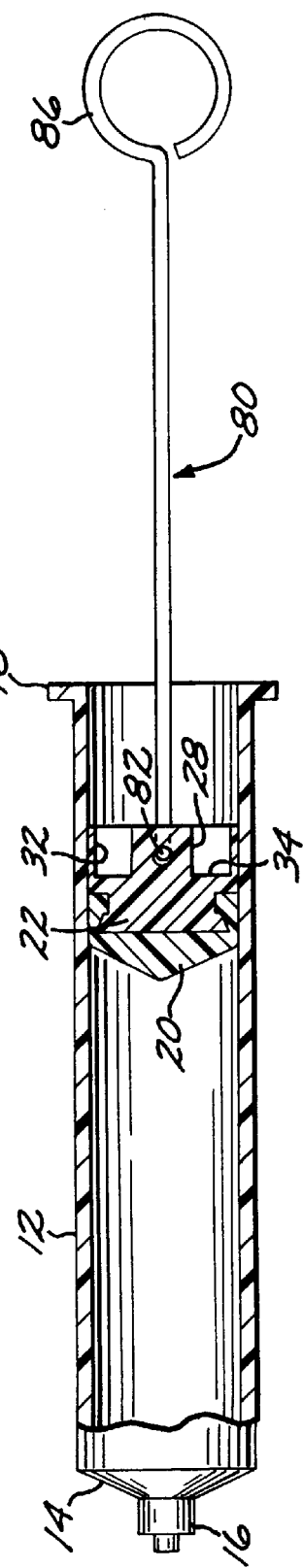

SPRING-ACTUATED INFUSION SYRINGE

CROSS-REFERENCE TO RELATED APPLICATION

Not Applicable

FEDERALLY FUNDED RESEARCH OR DEVELOPMENT

Not Applicable

BACKGROUND OF THE INVENTION

This invention relates generally to the field of liquid infusion devices for medical applications. More specifically, it relates to mechanically-driven infusion devices used for the administration of a liquid medicament to a patient from a filled syringe into an intravenous (IV) administration system.

Various devices have been developed for the intravenous (IV) infusion of liquid medicaments into a patient at a controlled flow rate over an extended period of time. For example, gravity flow IV administration sets have been employed for many years, and more recently, IV administration sets with electrically powered pumps have been developed.

There are applications in which a more compact and inexpensive type of infusion device is desired or required. For example, in addition to direct infusion from a syringe, it is frequently necessary to infuse a secondary fluid into a primary IV flow from a gravity flow or electrically-pumped IV administration set. Also, infusion into an ambulatory patient frequently requires an infusion device that is less bulky, less complex, and easier to use than gravity flow or pump-powered devices. For such applications, relatively complex self-powered infusion devices are frequently used.

With a typical, manually actuated IV administration syringe, infusion over an extended period of time is usually impractical or inconvenient. Furthermore, even among syringes of the same size from the same manufacturer, the actuation forces required to provide a given fluid flow-versus-time profile vary greatly from syringe to syringe. Consequently, it is necessary to provide a sufficiently high actuation force to achieve a substantial degree of uniformity in fluid delivery from syringe to syringe. It has proven difficult consistently to achieve such sufficiently high syringe actuation forces with manually actuated syringes.

To overcome these problems, the prior art has devised a variety of mechanisms for increasing the actuation force on the syringe throughout the infusion process. One type of syringe actuation mechanism is that which utilizes either internal or external springs to displace the plunger of the syringe. Examples of such mechanisms are shown in the following U.S. Pat. Nos.: 2,472,116—Maynes; 2,565,081—Maynes; 2,591,457—Maynes; 3,880,163—Ritterskamp; 3,882,863—Sarnoff et al.; 4,381,006—Genese; 4,530,695—Phillips et al.; 4,597,754—Thill et al.; 4,623,330—Laby et al.; 4,755,172—Baldwin; 4,966,585—Gangemi; 4,997,420—LeFevre; 5,078,679—Reese; 5,100,389—Vaillancourt; 5,178,609—Ishikawa; 5,318,539—O'Neil; 5,320,609—Haber et al.; 5,330,430—Sullivan; 5,383,858—Reilly et al.; and 5,599,315—McPhee. Another example is shown in European Patent Application Publication No. 584 569 A2.

The known prior art devices suffer from one or more shortcomings, however. For example, several of the above-listed patents show the use of "constant force" springs, which are elongated flat leaf springs coiled on a drum. Such springs, however, add expense, bulk, and mechanical complexity to the device.

Another drawback of some prior art devices is that a relatively great physical effort is required to compress the plunger actuation spring, because these devices lack a sufficient mechanical advantage to reduce the "loading effort" any appreciable degree. Other syringe actuation devices of the prior art require the syringe to be disconnected from any downstream fluid conduits (such as an IV administration set) before being loaded into the actuation device. This limitation makes such devices disadvantageous for use in those clinical applications, such as IV administration procedures, in which it is advantageous to load a pre-filled syringe into the syringe actuation device while the syringe is connected to the IV conduit.

It would therefore be a significant advancement over the prior art to provide a spring-actuated infusion syringe that overcomes the aforementioned limitations. Specifically, it would be advantageous to provide such a device that yields improved uniformity in syringe-to-syringe fluid flow rates without a mechanism of undue complexity. Furthermore, it would be advantageous to provide such a syringe that may be filled and spring-loaded without undue physical effort, and without disconnecting it from a downstream conduit.

SUMMARY OF THE INVENTION

Broadly, the present invention is a spring-actuated infusion syringe comprising a tubular barrel for holding a liquid medicament. The barrel has an open proximal end and a distal end portion that defines a fluid flow passage communicating with the interior of the barrel. A plunger disposed for axial translation in the barrel is engaged by a spring-loaded piston that drives the plunger distally into the barrel to express the contents of the barrel from the syringe.

More specifically, in accordance with a preferred embodiment of the invention, the syringe further comprises an internally-threaded hollow housing with an open distal end and a coil spring disposed longitudinally therein. The spring has a proximal end that is seated against an end cap forming a closed proximal end for the housing. The piston includes a hollow, tubular portion that receives the distal end of the spring, the latter seating against a spring seat at the distal end of the piston. The proximal end of the syringe barrel has an annular flange that functions as an external thread for engagement with the internal thread of the housing. The spring provides a distally-directed biasing force against the piston.

In use, the barrel of the syringe is filled with a medicament through the fluid flow passage in the distal end portion, and then the flow of medicament from the syringe is obstructed (for example, by a valve or a clamp or the like). The proximal end of the syringe barrel is inserted into the open distal end of the housing, and it is installed in the housing by threading the flange along the internal housing thread. When the barrel is inserted into the housing, the piston enters the proximal end of the barrel and seats against the plunger. As the barrel is threaded into the housing, the piston compresses the spring against the biasing force of the spring. The threading is stopped when the spring is compressed to the desired degree. Decompression of the spring is prevented by the hydrostatic pressure of the liquid within the barrel, which cannot be relieved due to the obstruction of the outflow of liquid from the barrel. The engagement between the annular barrel flange and the internal housing thread retains the barrel at the desired axial position within the housing.

When it is desired to deliver the liquid from the syringe into the infusion system, the obstruction is removed. The hydrostatic pressure on the liquid in the barrel being thereby relieved, the spring decompresses, its biasing force pushing the piston, and with it the plunger, distally into the syringe barrel. The movement of the plunger distally within the barrel displaces the liquid therefrom through the fluid flow passage in the distal tip portion of the barrel, and expresses the liquid as an outflow into the system.

The plunger is advantageously configured to facilitate the filling of the barrel with a liquid medicament provided from an external source or container. Specifically, a filling implement is provided, which comprises a rod with a handle at its proximal end and a hook at its distal end. The interior of the plunger is provided with a fitting that may be engaged by the hook. When the barrel is empty, with the plunger at its distal extreme of travel, the filling implement is inserted into the open proximal end of the barrel, and the hook is engaged with the fitting. With the barrel in fluid communication with a source of liquid medicament, the plunger is pulled proximally by means of the filling implement, thereby filling the barrel. When the barrel is filled, the hook is disengaged from the fitting, and the filling implement is removed from the barrel. The barrel is now ready for installation in the housing, as described above.

As will be seen from the foregoing summary, a spring-actuated syringe in accordance with the present invention provides sufficient syringe actuation force substantially to overcome non-uniformity in syringe-to-syringe operational characteristics, with a more nearly constant fluid flow rate as the syringe is emptied without the use of "constant force" springs and their attendant complexities. Furthermore, the syringe does not have to be disconnected from an infusion system in order to be loaded into a separate actuation device. In addition, the syringe can be filled without having to overcome the force of the spring, since the spring is removed from the barrel during the filling process. Moreover, the spring-actuated syringe is compact in size and simple to operate. Still further, it can be manufactured at sufficiently low cost so as to be disposable. These and other advantages will be more fully appreciated from the detailed description that follows.

BRIEF DESCRIPTION OF THE DRAWINGS

FIG. 1 is an axial cross-sectional view of a spring-actuated infusion syringe in accordance with a preferred embodiment of the invention, showing a filled syringe at the beginning of the spring-loading process;

FIG. 2 is an axial cross-sectional view, similar to that of FIG. 1, showing a filled syringe at the conclusion of the spring-loading process;

FIG. 3 is an axial cross-sectional view, similar to that of FIGS. 1 and 2, showing the syringe after its contents have been discharged;

FIG. 4 is a cross-sectional view taken along line 4—4 of FIG. 1;

FIG. 5 is an exploded perspective view of the plunger assembly and the piston of the syringe;

FIG. 6 is an axial cross-sectional view of the syringe barrel and plunger, with a filling attachment attached to the plunger prior to filling the barrel; and FIG. 7 is an axial cross-sectional view, similar to that of FIG. 6, showing the position of the plunger and the filling attachment after the barrel has been filled.

DETAILED DESCRIPTION OF THE PREFERRED EMBODIMENT

Referring now to the drawings, and specifically to FIGS. 1 through 5, a spring-actuated syringe 10, in accordance with a preferred embodiment of the invention, is shown. The syringe 10 comprises a hollow, tubular barrel 12 having a tapered, conical distal tip portion 14 that defines a fluid flow passage 15 (FIG. 3) that communicates with the interior of the barrel 12. The distal tip portion terminates in a fitting 16 that is adapted for connection to a fluid conduit 17 (FIG. 6), of the type commonly used in infusion systems. The barrel 12 has an open proximal end surrounded by an annular flange 18.

Disposed within the barrel 12 for longitudinal (axial) translation therein is a plunger assembly, comprising a conical plunger tip 20, formed of an elastomeric material, attached to a more rigid plunger core 22. The attachment of the plunger tip 20 to the plunger core 22 may be by means of an annular lip 24 on the tip 20 that is received by, and frictionally crimped into, a mating annular groove 26 in the core 22, as best shown in FIG. 5. The plunger core 22 includes proximally-extending central projection 28 that has a transverse bore 30. A peripheral rim 32 coaxially surrounds the projection 28, thereby defining an annular surface 34 between the projection 24 and the rim 32, as best shown in FIGS. 6 and 7.

The syringe 10 further comprises a hollow, cylindrical housing 36 having a distal end opening 37 and an open proximal end. The interior surface of the housing 36 adjacent the proximal end is provided with an internal thread 38 that mates with an external thread 40 on an end cap 42 which closes the proximal end of the housing 36, and which thus defines a proximal end wall. A major portion of the interior surface of the housing 36, extending proximally from its distal end, is formed with a continuous helical land 44 that defines a continuous helical groove 45 that functions as a relatively large-pitched internal thread. The inside diameter of the distal opening 37 is sufficiently large to permit the flange 18 at the proximal end of the barrel 12 to be threaded into the housing 36 by cooperation with the helical groove 45. Thus, the barrel 12 is retained at a selected axial position within the housing 36 by means of the threaded engagement between the flange 18 and the helical groove 45.

Extending distally from the interior surface of the end cap 42 is a first or proximal spring guide 46. The proximal spring guide 46 is a hollow, tubular member that is joined to the interior surface of the end cap 42 by a cylindrical base portion 48. The proximal portion of a coil spring 50 is coaxially carried around the proximal spring guide 46, with the proximal end of the coil spring 50 seating against the proximal end wall defined by the interior surface of the end cap 42, around the base portion 48 of the proximal spring guide 46.

The exterior surface of the end cap 42 has a central pocket 52 that communicates with the hollow interior of the proximal spring guide 46 by means of a narrow passage 54 through the base portion 48. The proximal end of a flexible, filamentous tether 56 is passed through the passage 54 into the pocket 52, where a proximal retention knob 58, preferably a copper stamping or the like, is crimped onto the proximal end of the tether 56. The tether 56 is preferably a length of braided stainless steel wire, although other types of metal wire, and perhaps some types of polymeric filament, may serve.

The distal end of the tether 56 is secured to a piston 60 that provides a seat for the distal end of the coil spring 50. The piston 60 is a hollow, tubular member with an open proximal end, and it is disposed coaxially within the housing 36 for axial translation therein. The piston 60 has an outside diameter that is slightly smaller than the inside diameter of the barrel 12 so that it is slidably received within the barrel 12, through the open proximal end of the barrel 12, for axial translation therein. The piston 60 has an annular distal end wall 62 (best shown in FIG. 4) against which the distal end of the coil spring 50 is seated. Extending proximally into the interior of the piston 60 from the distal end wall 62 is a central cylindrical member 64. The cylindrical member 64 functions as a distal spring guide that coaxially carries the distal end of the coil spring 50. The distal spring guide 64 has a hollow interior that defines a chamber 66 that is accessed by a narrow axial passage 68 through the proximal wall of the distal spring guide 64.

The distal end of the tether 56 passes through the open proximal end of the piston 60. It is then passed though the axial passage 68 and secured within the chamber 66 by a distal retention knob 70, similar to the proximal retention knob 58, that is crimped onto it. The spring 50 urges the piston 60 distally toward the open distal end of the housing 36. The length of the tether 56 is selected so as to limit the travel of the piston 60 so that, at its distal limit of travel, no more than about one-third to one-half of the axial length of the piston 60 extends out of the open distal end of the housing 36, as shown in FIG. 1.

The distal end of the distal spring guide 64 is configured so as to define a central recess 72. This central recess 72 receives the central projection 28 of the plunger core 22. The distal portion of the piston 60 is of a slightly smaller outside diameter than the rest of the piston 60, thereby defining a peripheral seat 74 that receives the peripheral rim 32 of the plunger core 22. There is thus an intimate engagement between the plunger core 22 and the piston 60.

FIGS. 6 and 7 illustrate the initial steps in the method of using the syringe 10. With the barrel 12 removed from the housing 36, and with the plunger assembly 20, 22 at its distal limit of travel, the distal barrel fitting 16 is connected to one end of the fluid conduit 17, the other end of which is in fluid communication with a medicament source 76. A filling implement 80 is inserted into the open proximal end of the barrel 12, and it is engaged with the plunger assembly 20, 22 to fill the barrel 12 through the conduit 17. The filling implement 80 comprises an elongate rod 82 having an angled or hooked distal end 84 and a proximal end formed into a grip or handle 86. As shown in FIG. 6, the hooked distal end 82 of the filling implement is inserted through the transverse bore 30 of the plunger core projection 28. Using the filling implement 80, a practitioner pulls the plunger assembly 20, 22 proximally, thereby drawing the medicament into the barrel 12 through the fluid flow passage 15 in the distal tip portion 16. When the barrel 12 is filled, the plunger is at or near its proximal limit of travel, as shown in FIG. 7. At this point, the filling implement 80 is disengaged from the plunger assembly 20, 22, and removed from the barrel 12. Outflow of the contents of the barrel is prevented by obstructing the conduit 17, by means such as a clamp (not shown) or a valve (not shown).

Referring again to FIG. 1, the proximal end of the barrel 12 is inserted into the distal opening 37 of the housing 36. The insertion of the barrel 12 into the housing 36 brings the plunger core 22 into engagement with the piston 60, as described above. The proximal flange 18 of the barrel 12 engages the internal helical groove 45, so that the barrel 12 may be threaded into the housing 36. The fluid in the barrel 12, being obstructed from outflow, is incompressible. Thus, by threading the barrel 12 into the housing 60, the piston 60 is pushed proximally by the plunger assembly 20, 22 against the force of the spring 50, thereby compressing the spring 50, as shown in FIG. 2. The spring is maintained in a compressed state by the hydrostatic pressure of the fluid contained in the syringe barrel 12.

When fluid outflow from the barrel is permitted (i.e., by removing the obstruction from the conduit), the hydrostatic pressure applied by the fluid is relieved, thereby allowing the spring 50 to decompress. The decompressing spring 50 urges the piston 60, and thus the plunger assembly 20, 22, toward the distal end of the barrel, as shown in FIG. 3, thereby displacing the fluid from the barrel 12 through the fluid flow passage 15 in the distal tip portion 16.

When the barrel 12 is empty, it is merely threaded out of the housing 36. The piston 60 is retained at least partially within the housing 36 by means of the tether 56.

The degree of compression of the spring 50, and thus the force it exerts on the piston 60 and the plunger assembly 20, 22, may be adjusted by threading the end cap 42 into or out of the proximal end of the housing. This threading action may be facilitated by means on the exterior surface of the end cap for receiving a tool (not shown) for turning the end cap. For example, the pocket 52 in the exterior of the end cap 42 may be dimensioned and configured to receive a hex key, or a screwdriver blade, or the like.

There has thus been described a novel spring-actuated syringe that provides the benefits of spring-actated syringes with a structure that is simpler and more economical to manufacture than prior art springactuated syringes. Thus, a syringe in accordance with the present invention may be made as a disposable assembly. Furthermore, the syringe may filled and spring-loaded without undue physical effort, and without disconnecting it from an infusion system.

While a preferred embodiment of the invention has been described herein, it will be appreciated that a number of modifications and variations may suggest themselves to those skilled in the pertinent arts. For example, the configuration of the housing and the spring are exemplary only, as is the structure of the piston, the plunger, and the filling implement. Such modifications and variations should therefore be considered within the spirit and scope of the present invention, as defined in the claims that follow.

What is claimed is:

1. A spring-actuated syringe, comprising:
   a housing having an open distal end and a proximal end terminated by a proximal end wall;
   a piston disposed in the housing for axial translation therein;
   a tether connecting the piston to the proximal end of the housing;
   a spring disposed longitudinally in the housing between the piston and the proximal end wall of the housing so as to bias the piston toward the distal end of the housing;
   a barrel for the containment of a liquid medicament, the barrel having a distal end portion having a fluid flow passage therethrough and an open proximal end, the proximal end of the barrel being axially insertable in the housing through the open distal end of the housing, whereby the piston is received in the barrel through the proximal end of the barrel when the barrel is inserted into the housing;
   a plunger disposed in the barrel for axial translation therein, the plunger being engaged by the piston when the piston is received in the barrel; and
   retention means, operable between the barrel and the housing, for retaining the barrel at a selected axial position in the housing when the barrel is inserted axially into the housing.

2. The syringe of claim 1, wherein the tether passes through the length of the spring.

3. The syringe of claim 1, wherein the tether is a filamentous element.

4. The syringe of claim 1, wherein the retention means comprises:

an internal thread in the housing; and a peripheral flange around the proximal end of the barrel that is engageable with the internal thread, whereby the barrel is threadable into the housing to a selected axial position.

5. The syringe of claim 1, further comprising means for adjusting the bias force applied by the spring to the piston.

6. The syringe of claim 5, wherein the means for adjusting the bias force comprises:

an end cap in the proximal end of the housing, the end cap including the proximal end wall of the housing; and means for adjusting the axial position of the end cap in the housing.

7. The syringe of claim 6, wherein the means for adjusting the axial position of the end cap comprises:

an internal thread in the proximal end of the housing; and an external thread on the end cap that is engageable with the internal thread in the proximal end of the housing.

8. The syringe of claim 1, wherein the plunger is engageable through the proximal end of the barrel so as to be pulled from the distal end of the barrel toward the proximal end thereof.

9. A spring-actuated syringe, comprising:

a housing having an open distal end and a proximal end terminated by a proximal end wall;

a spring-biased piston disposed in the housing for axial translation therein, the piston being biased toward the distal end of the housing;

a filamentous tether connecting the piston to the proximal end wall of the housing;

a barrel for the containment of a liquid medicament, the barrel having a distal end with a fluid flow passage therethrough and an open proximal end, the proximal end of the barrel being axially insertable in the housing trough the open distal end of the housing, whereby the piston is received in the barrel through the proximal end of the barrel when the barrel is inserted into the housing;

a plunger disposed in the barrel for axial translation therein, the plunger being engaged by the piston when the piston is received in the barrel; and retention means, operable between the barel and the housing, for retaining the barrel at a selected axial position in the housing when the barrel is inserted axially into the housing.

10. The syringe of claim 9, wherein the piston is spring-biased by a bias force applied by a coil spring disposed axially in the housing.

11. The syringe of claim 10, wherein the tether passes through the length of the spring.

12. The syringe of claim 10, further comprising means for adjusting the bias force applied by the spring to the piston.

13. The syringe of claim 12, wherein the spring has a proximal end seated against the proximal end wall of the housing, and wherein the means for adjusting the bias force comprises:

an end cap in the proximal end of the housing, the end cap including the proximal end wall of the housing; and means for adjusting the axial position of the end cap in the housing.

14. The syringe of claim 13, wherein the means for adjusting the axial position of the end cap comprises:

an internal thread in the proximal end of the housing; and an external thread on the end cap that is engageable with the internal thread in the proximal end of the housing.

15. The syringe of claim 9, wherein the retention means comprises:

an internal thread in the housing; and a peripheral flange around the proximal end of the barrel that is engageable with the internal thread, whereby the barrel is threadable into the housing to a selected axial position.

16. The syringe of claim 9, wherein the plunger is engageable through the proximal end of the barrel so as to be pulled from the distal end of the barrel toward the proximal end thereof.

* * * * *